(12) United States Patent
Brown et al.

(10) Patent No.: US 7,017,591 B2
(45) Date of Patent: Mar. 28, 2006

(54) PARTICULATE COATED MONOFILAMENT DEVICES

(75) Inventors: Dale G. Brown, Wharton, TX (US); Michael Schweigert, Stafford, TX (US)

(73) Assignee: International Tape Partners LLC, Stafford, TX (US)

( * ) Notice: Subject to any disclaimer, the term of this patent is extended or adjusted under 35 U.S.C. 154(b) by 0 days.

(21) Appl. No.: 10/334,089

(22) Filed: Dec. 30, 2002

(65) Prior Publication Data

US 2003/0200983 A1 Oct. 30, 2003

Related U.S. Application Data

(63) Continuation-in-part of application No. 09/935,920, filed on Aug. 23, 2001, now Pat. No. 6,545,077, and a continuation-in-part of application No. 09/935,921, filed on Aug. 23, 2001, now Pat. No. 6,609,527, and a continuation-in-part of application No. 09/935,910, filed on Aug. 23, 2001, now Pat. No. 6,575,176.

(51) Int. Cl.
*A61C 15/00* (2006.01)

(52) U.S. Cl. .................................... 132/321
(58) Field of Classification Search ............... 132/321; 424/49, 50, 401
See application file for complete search history.

(56) References Cited

U.S. PATENT DOCUMENTS

| | | | |
|---|---|---|---|
| 35,439 A | 6/1862 | Fraser | |
| 3,153,418 A | 10/1964 | Fleming | 132/93 |
| 3,491,776 A | 1/1970 | Fleming | 132/321 |
| 3,664,915 A | 5/1972 | Gore | 161/164 |
| 3,699,979 A | 10/1972 | Muhler et al. | 132/89 |
| 3,800,812 A | 4/1974 | Jaffe | 132/89 |
| 3,837,351 A | 9/1974 | Thornton | 132/89 |
| 3,942,539 A | 3/1976 | Corliss et al. | 132/79 |
| 3,953,566 A | 4/1976 | Gore | 264/288 |
| 3,962,153 A | 6/1976 | Gore | 260/2.5 R |
| 4,096,227 A | 6/1978 | Gore | 264/210 R |
| 4,187,390 A | 2/1980 | Gore | 174/102 R |
| 4,256,806 A | 3/1981 | Snyder | 428/378 |
| 4,385,093 A | 5/1983 | Hubis | 428/316.6 |
| 4,478,665 A | 10/1984 | Hubis | 156/229 |
| 4,776,358 A | 10/1988 | Lorch | 132/321 |
| 4,795,421 A | 1/1989 | Blasius, Jr. et al. | 604/1 |
| 4,911,927 A * | 3/1990 | Hill et al. | 424/443 |
| 4,974,615 A | 12/1990 | Doundoulakis | 132/321 |
| 4,986,288 A | 1/1991 | Kent et al. | 132/321 |
| 5,033,488 A | 7/1991 | Curtis et al. | 132/321 |
| 5,057,310 A | 10/1991 | Hill et al. | 424/52 |
| 5,098,711 A | 3/1992 | Hill et al. | 424/401 |
| 5,165,913 A | 11/1992 | Hill et al. | 424/49 |
| 5,209,251 A | 5/1993 | Curtis et al. | 132/321 |
| 5,219,572 A | 6/1993 | Sivaramakrishnan et al. | 424/438 |
| 5,220,932 A | 6/1993 | Blass | 132/321 |
| 5,357,990 A | 10/1994 | Suhonen et al. | 132/321 |
| 5,433,226 A | 7/1995 | Burch | 132/321 |
| 5,479,952 A | 1/1996 | Zachariades et al. | 132/321 |
| 5,503,842 A | 4/1996 | Fazan et al. | 260/621 |
| 5,518,012 A | 5/1996 | Dolan et al. | 132/321 |
| 5,538,667 A | 7/1996 | Hill et al. | 252/312 |
| 5,616,315 A * | 4/1997 | Masterman et al. | 424/54 |
| 5,651,959 A | 7/1997 | Hill et al. | 424/49 |
| 5,697,390 A | 12/1997 | Garrison et al. | 132/321 |
| 5,711,935 A | 1/1998 | Hill et al. | 424/49 |
| 5,718,251 A | 2/1998 | Gray et al. | 132/321 |

(Continued)

Primary Examiner—Todd E. Manahan

(57) ABSTRACT

Disclosed are coated monofilament dental devices overcoated with biofilm-responsive particulate abrasives.

21 Claims, 8 Drawing Sheets

U.S. PATENT DOCUMENTS

| | | | |
|---|---|---|---|
| 5,755,243 A | 5/1998 | Roberts et al. | 132/321 |
| 5,760,117 A | 6/1998 | Chen | 524/270 |
| 5,765,576 A | 6/1998 | Dolan et al. | 132/321 |
| 5,787,758 A | 8/1998 | Sheldon | 74/490 |
| 5,845,652 A | 12/1998 | Tseng et al. | 132/200 |
| 5,848,600 A | 12/1998 | Bacino et al. | 132/321 |
| 5,875,798 A | 3/1999 | Petrus | 132/321 |
| 5,884,639 A | 3/1999 | Chen | 132/321 |
| 5,911,228 A | 6/1999 | Curtis et al. | 132/321 |
| 5,918,609 A | 7/1999 | Tsao et al. | 132/321 |
| 5,962,572 A | 10/1999 | Chen | 524/474 |
| 5,967,153 A | 10/1999 | Mitha et al. | 132/321 |
| 5,967,154 A | 10/1999 | Anderson | 132/321 |
| 5,988,444 A | 11/1999 | Williams et al. | 222/137 |
| 5,998,431 A | 12/1999 | Tseng et al. | 514/300 |
| 6,003,525 A | 12/1999 | Katz | 132/321 |
| 6,027,592 A | 2/2000 | Tseng et al. | 156/167 |
| 6,080,481 A | 6/2000 | Ochs et al. | 428/372 |
| 6,083,208 A | 7/2000 | Modak et al. | 604/265 |
| 6,148,830 A | 11/2000 | Chen | 132/321 |
| 6,161,555 A | 12/2000 | Chen | 132/321 |
| 6,192,896 B1 | 2/2001 | Tsao et al. | 132/321 |
| 6,371,133 B1 * | 4/2002 | Gant | 132/321 |

* cited by examiner

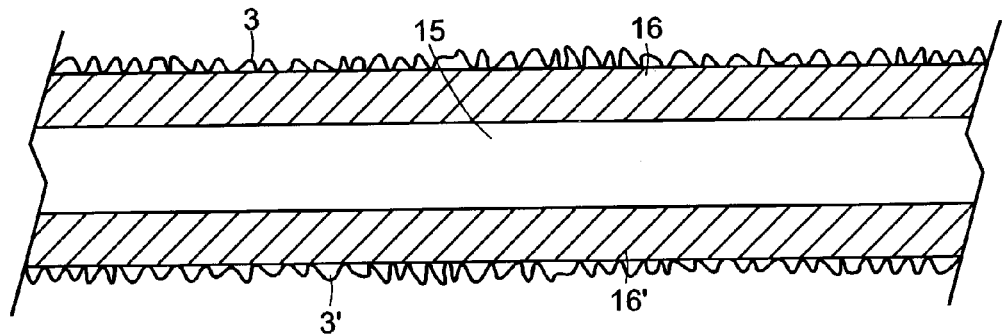
FIG. 4
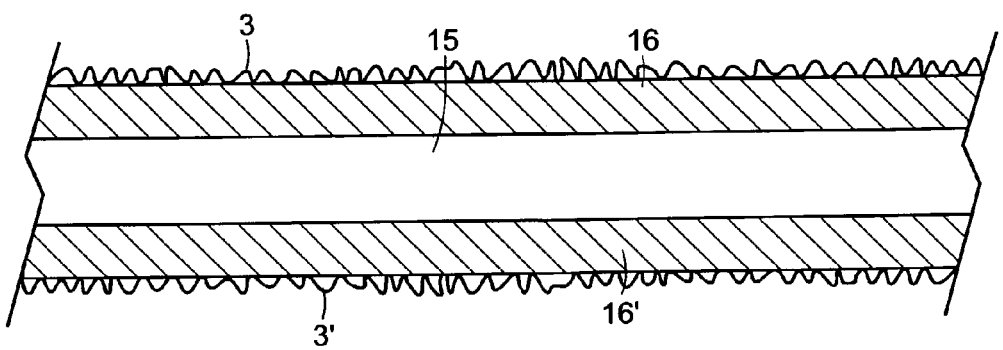

PARTICULATE COATED MONOFILAMENT DEVICES

CROSS-REFERENCE TO RELATED APPLICATIONS

This application is a continuation-in-part of U.S. patent applications, Ser. No. 09/935,920 now U.S. Pat. No. 6,545,077; Ser. No. 09/935,921 now U.S. Pat. No. 6,609,527; Ser. No. 09/935,910 now U.S. Pat No. 6,575,176, each filed 23 Aug. 2001, and entitled respectively, "Monofilament dental tapes with substantive coatings"; "Non-crystalline saliva soluble coatings for elastomeric monofilament tapes"; and "Monofilanient dental tapes with soft abrasive coatings." This application is copending with U.S. patent applications, Ser. Nos. 10/331,800 and 10/331,795, each filed on the same date as this application and entitled, respectively, "Coated Multifilanient Dental Devices Overcoated with linbedded Particulate" and "Coated Micromesh Dental Devices Overcoated with Imbedded Particulate. The disclosures of these applications are hereby incorporated herein by reference.

BACKGROUND OF THE INVENTION

Dental floss is defined in *Webster's New World Dictionary*, 1983, as " . . . thread for removing food particles between the teeth."

The concept of using dental floss for cleansing interproximal spaces appears to have been introduced by Parmly in 1819, *Practical Guide to the Management of Teeth,* Cullins & Croft Philadelphia, Pa. Numerous types of floss were developed and used for cleaning interproximal and subgingival surfaces, until finally in 1948 Bass established the optimum characteristics of dental floss, *Dental Items of Interest,* 70, 921–34 (1948).

Bass cautioned that dental floss treated with sizing, binders and/or wax produces a "cord" effect as distinguished from the desired "spread filament effect". This cord effect reduces flossing efficiency dramatically and visually eliminates splaying (i.e., the flattening and spreading out of filaments) necessary to achieve the required interproximal and subgingival mechanical cleaning. This cleaning is then required to be followed by the entrapment and removal of debris, plaque and microscopic materials from interproximal spaces by the "spread" floss as it is removed from between teeth.

Proper use of dental floss is necessary to clean the considerable surface area on the interproximal surfaces of teeth, which cannot usually be reached by other cleaning methods or agents, e.g., the bristles of a toothbrush, the swishing action of a rinse, or by the pulsating stream from an oral irrigator.

Historically, the purpose of dental floss was to:
(1) dislodge and remove any decomposing food material, debris, etc., that has accumulated at the interproximal surfaces, which could not be removed by other oral hygiene means, and
(2) dislodge and remove as much as possible the growth of bacterial material (plaque, tartar, calculus) that had accumulated there since the previous cleaning.

Effective oral hygiene requires that three control elements be maintained by the individual:
(1) Physical removal of stains, plaque and tartar. This is accomplished in the strongest sense by scraping and abrasion in the dentist's office. Self administered procedures are required frequently between visits and range from tooth brushing with an appropriate abrasive toothpaste through flossing and water jet action down to certain abrasive foods and even the action of the tongue against tooth surfaces.
(2) Surfactant Cleaning. This is required to remove: food debris and staining substances before they adhere to the tooth surface; normal dead cellular (epithelial) material which is continually sloughed off from the surfaces of the oral cavity and microbial degradation products derived from all of the above. Besides the obvious hygienic and health benefits related to simple cleanliness provided by surfactants, there is an important cosmetic and sense-of-well-being benefit provided by surfactant cleansing. Research has shown that the primary source of bad breath is the retention and subsequent degradation of dead cellular material sloughed off continuously by the normal, healthy mouth.
(3) Frequency of Cleansing. This is perhaps the most difficult to provide in today's fast-paced work and social environment. Most people recognize that their teeth should be brushed at least 3 times a day and flossed at least once a day. The simple fact is that most of the population brush once a day, some brush morning and evening, but precious few carry toothbrush and dentifrice to use the other three or four times a day for optimal oral hygiene. Consumer research suggests that the population brushes an average of 1.3 times a day. Most surprising, less than 15% of adults floss regularly. Reasons offered for not flossing: difficult to do, painful, not effective, doesn't seem to do anything, and leaves a bad taste.

Most commercial interproximal devices marketed at the present time contain various coatings of wax or wax like substances that function as: binders for the various multifilament flosses to minimize fraying, lubricants, flavor carriers, and/or fluoride carriers. When added to various monofilament dental tapes, generally at substantially lower levels, wax functions as a lubricant and/or flavor/active ingredient carrier.

An almost universal shortcoming common to most waxed dental flosses and to all coated monofilament dental tapes is the user perception during flossing that the dental floss or dental tape is "not working" and/or "not cleaning", etc.

In fact, most of these devices have only marginal efficacy with respect to removing biofilms (plaque). Biofilms generally require physical abrasive-type action to be effectively removed. Periodic professional cleaning is a recommended means for effectively controlling biofilm formation.

The classification of plaque as a biofilm is considered a major advance in the development of more effective "self-treatment" oral care products. See the following biofilm references:

Greenstein and Polson, *J. Periodontol.,* May 1998, 69:5: 507–520; van Winkelhoff, et al., *J. Clin. Periodontol.,* 1989, 16:128–131; and Wilson, *J. Med. Microbiol.,* 1996, 44:79–87.

Biofilms are defined as " . . . matrix-enclosed bacterial population adherent to each other and to the surface or intersurfaces. These masses secrete an exopolysaccharide matrix for protection. Considerably higher concentrations of drugs are needed to kill bacteria in biofilms than organisms in aqueous suspensions."

Costerton, J. W., Lewandowski, Z., DeBeer, D., Caldwell, D., Korber, D., James, G. Biofilms, the customized microniche. *J. Bacterio.,* 1994, 176:2137–2142.

The unique attributes of biofilms is being recognized as increasingly important in the 1990's. Future studies into the mode of growth of biofilms will allow manipulation of the bacterial distribution.

Douglass, C. W., Fox, C. H. Cross-sectional studies in periodontal disease: Current status and implications for dental practice. *Adv. Dent. Res.*, 1993, 7:26–31.

The number of adults over 55 who will need periodontal services will increase. The type of services will need to be adjusted to meet the need.

Greenstein, G. J., Periodontal response to mechanical non-surgical therapy: A review. *Periodontol.*, 1992, 63:118–130.

Mechanical therapy remains effective with caveats of compliance and skill of therapists.

Marsh, P. D., Bradshaw, D. J. Physiological approaches to the control of oral biofilms. *Adv. Dent. Res.*, 1997, 11:176–185.

Most laboratory and clinical findings support the concept of physiological control.

Further studies will reveal details of biofilm diversity.

Page, R. C., Offenbacher, S., Shroeder, H., Seymour, G. J., Kornman, K. S. Advances in the pathogenesis of periodontitis: Summary of developments, clinical implications and future directions. *Periodont. 2000*, 1997, 14:216–248.

Genetic susceptibility to three oral anaerobic bacteria play an important part in the progression of periodontitis. Acquired and environmental risk factors exacerbate the problem. Mechanical disruption will remain an effective and essential part of periodontal therapy.

Papapanou, P. N., Engebretson, S. P., Lamster, I. B. Current and future approaches for diagnosis of periodontal disease. *NY State Dent. J.*, 1999, 32–39.

New techniques are available such as a novel pocket depth measurement device, microscopic techniques, immunoassay, DNA probes, BANA hydrolysis tests. These more clearly define the nature of periodontitis.

SUMMARY OF THE INVENTION

The present invention is directed to biofilm-responsive, coated monofilament dental tapes suitable for physical-abrasive-type removal, disruption and/or control of biofilms that form on interproximal and/or subgingival tooth surfaces not reachable by brushing or rinsing. The coated monofilament dental tapes of the present invention are overcoated with a particulate abrasive that remains substantive to the monofilament tape base coating until said base coating is released during flossing. During flossing, the particulate abrasive overcoating of the present invention separates from the released base coating to work in conjunction with the dental tape. That is, the released particulate abrasive cooperates with the monofilament dental tape as the tape is being worked interproximally and subgingivally to deliver physical-abrasive-type cleaning, disruption and/or control of biofilms formed on interproximal and subgingival tooth surfaces.

The physical-abrasive-type cleaning, disruption and/or control of biofilms achieved with the particulate abrasive overcoated monofilament dental tapes of the present invention continues until:
  the monofilament dental tape is removed from the space and flossing of the area is discontinued,
  the particulate abrasive dissolves and/or is washed away, and/or
  the biofilm is physically removed, disrupted and/or controlled.

The physical-abrasive-type cleaning, disruption and/or control of biofilms with the particulate abrasive overcoated monofilament dental tapes of the present invention can be simultaneously improved further with a chemotherapeutic treatment of the particulate abrasive monofilament tape effected biofilm by various chemotherapeutic substances contained in the base coating and/or in the particulate overcoating, which chemotherapeutic substances are released onto the tooth surfaces during flossing along with the particulate abrasive.

Accordingly, one embodiment of the present invention comprises biofilm-responsive monofilament dental tape devices.

A further embodiment of the present invention comprises coated monofilament dental tape devices with releasable particulate abrasives that are biofilm-responsive during flossing.

Another embodiment of the invention comprises a self-treatment means for routinely removing, disrupting and/or controlling biofilms formed on interproximal and subgingival tooth surfaces.

Still another embodiment of the invention comprises a method for overcoating coated monofilament dental tapes with releasable particulate abrasives of various particle sizes and particle size distributions, in order to remove, disrupt and/or control biofilms.

Yet another embodiment of the invention comprises a method for removing, disrupting and/or controlling biofilms that form on interproximal and subgingival tooth surfaces.

A further embodiment of the invention comprises biofilm-responsive monofilament dental devices overcoated with particulate abrasives and containing a saliva soluble base coating which contains an antimicrobial.

Another embodiment of the invention comprises biofilm-responsive monofilament dental devices overcoated with active particulate abrasives such as whitening and tartar control abrasives.

Still another embodiment of the invention comprises biofilm-responsive monofilament dental devices overcoated with dental particulate abrasives including silica, pumice, alumina, calcium carbonate and dicalcium phosphate dihydrate.

Yet another embodiment of the invention comprises biofilm-responsive, monofilament dental devices overcoated with imbedded particulate abrasives, where said abrasives contain other substances ranging from flavorants, antimicrobials and cleaning substances to mouth conditioners and various pharmaceutical substances.

A further embodiment of the invention comprises improved waxed monofilament dental tapes with an overcoating of imbedded particulate abrasive.

Still another embodiment of the invention comprises improved waxed monofilament dental tapes with overcoatings of imbedded particulate abrasive and saliva soluble particulate substances containing flavorant and mouth conditioning substances.

Another embodiment of the invention comprises improved waxed monofilament dental tapes with an overcoating of imbedded particulate abrasive containing a saliva soluble, substance containing flavorant and mouth conditioners.

Yet another embodiment of the invention comprises a method for improving monofilament dental tapes comprising sequential overcoating of said base coated monofilament dental tapes with two or more particulates having substantially different densities, wherein said various particulates are imbedded into the base coating prior to cooling and solidifying said base coating.

Still another embodiment of the invention comprises improved commercial, emulsion coated monofilament dental tape with an overcoating of imbedded particulate abrasive.

For purposes of describing the present invention, the following terms are defined as set out below:

"Monofilament dental devices" are defined as interproximal dental devices such as monofilament dental tape constructed of a single continuous monofilament, which can be extruded, slit from a film, etc. Examples of these devices are described in the following U.S. patents:

| | | | | | |
|---|---|---|---|---|---|
| Re. 35,439; | 3,800,812; | 4,974,615; | 5,760,117; | 5,433,226; | 5,479,952; |
| 5,503,842; | 5,755,243; | 5,845,652; | 5,884,639; | 5,918,609; | 5,962,572; |
| 5,998,431; | 6,003,525; | 6,083,208; | 6,198,830; | 6,161,555; | 6,027,192; |
| 5,209,251; | 5,033,488; | 5,518,012; | 5,911,228; | 5,220,932; | 4,776,358; |
| 5,718,251; | 5,848,600; | 5,787,758; | and | 5,765,576, | | the disclosures of which are hereby incorporated by reference.

Preferred monofilament dental devices include polytetrafluoroethylene (PTFE), polyethylene, polypropylene, etc., devices.

Particularly preferred monofilament dental devices include elastomeric monofilament dental devices such as detailed in Tables 3 through 7 below and described and claimed in the co-pending Patent Application entitled, "Elastomeric monofilament dental tapes," filed Aug. 23, 2001, which is hereby incorporated by reference.

"Coatings" for the monofilament dental devices are defined as those substances that coat monofilament dental devices for purposes of: lubrication and ease of tape insertion for carrying flavors and other additives, providing "hand" so the device can be wound around the fingers, etc. Preferred coatings include those emulsion coatings described in the following U.S. Pat. Nos. 4,950,479; 5,032,387; 5,538,667; 5,561,959; and 5,665,374, which are hereby incorporated by reference.

Particularly preferred coatings include those saliva soluble coatings for monofilament dental tapes described and claimed in co-pending U.S. patent application Ser. Nos. 09/935,922; 09/935,920; 09/935,921 and 09/935,710, all filed on Aug. 23, 2001, which are hereby incorporated by reference. Particularly preferred coatings are the crystal-free coatings described in Tables 8 and 9 below.

"Particulate abrasives" are defined as saliva soluble, semi-soluble and insoluble abrasive substances having a wide range of particle sizes and particle size distribution.

Preferred particulate abrasives include various inorganics such as glass beads, and various organics such as particles of polyethylene, polypropylene, etc.

Particularly preferred inorganic particulate abrasives include various dental abrasives such as: pumice, silica, alumina, silicon dioxide, magnesium oxide, aluminum hydroxide, diatomaceous earth, sodium potassium aluminum silicate, zirconium silicate, calcium carbonate, calcium silicate, fumed silica, hydrated silica, dicalcium phosphate dihydrate, anhydrous dicalcium phosphate, sodium tripolyphosphate, etc. See also Table 1 below.

Particularly preferred "active" particulate abrasives include:

peroxides such as: carbamide peroxide, calcium peroxide, sodium perborate, sodium percarbonate, magnesium peroxide, sodium peroxide, etc.;

phosphates such as: sodium hexametaphosphate, tricalcium phosphate, etc.; and pyrophosphates such as: tetrasodium pyrophosphate, tetrapotassium pyrophosphate, sodium acid pyrophosphate, calcium pyrophosphate, etc. See also Table 2 below. See also the following relevant U.S. patents: U.S. Pat. Nos. 6,221,341; 3,491,776; 3,330,732; 3,699,979; 2,700,636; 5,220,932; 4,776,358; 5,718,251; 5,848,600; 5,787,758; and 5,765,576.

"Releasable" particulate abrasive is defined as the property whereby particulate abrasive, which is adhered to the base coating of monofilament dental tape, remains substantive to said base coating until flossing begins, at which time the particulate abrasive separates from the saliva soluble base coating and remains available interproximally and subgingivally to work with the monofilament tape, responding to biofilms encountered on subgingival, interproximal and supragingival tooth surfaces with physical-abrasive-type cleaning.

"Particulate abrasive load" is defined as the percent by weight of particulate abrasive contained on the coated monofilament dental device as a percent by weight of the device. See Tables 1, 2 and 9 below.

"Base coat monofilament device load" is defined as the percent by weight of the base coating contained on the monofilament device as a percent by weight of the coated monofilament device.

"Total coating load" is defined as the percent by weight of the base coating plus the particulate abrasive overcoating contained on the monofilament device as a percent by weight of the device.

"Perceived Abrasive Factor (PAF)" is defined as the subjective level of perceived abrasivity when:

(1) winding the coated monofilament device around the fingers (i.e., "hand"), and (2) when working the device across tooth surfaces with a sawing action.

PAF grades range from 0 through 4, i.e., imperceptible (0), slightly perceptible (1), perceptible (2), very perceptible (3) and very abrasive (4). See Tables 1, 2 and 9 below. PAF values of about 2 or greater are preferred. PAF values above 3 are particularly preferred.

"Incidental Release Factor (IRF)" is defined as the percent by weight of the particulate abrasive retained on the coated monofilament dental device, when an 18 inch piece of the device is removed from a dispenser and wrapped around two fingers prior to flossing. (See Tables 1, 2 and 9.)

"Biofilm responsive" is defined as the property of particulate abrasives to work cooperatively with monofilament dental tapes and other cleaning and/or chemotherapeutic substances in the base coating to remove, disrupt and/or control biofilms when released from the coated monofilament tapes during flossing.

"Fluidized bed" is defined as a means of converting solid particulate abrasives into an expanded, suspended, solvent-free mass that has many properties of a liquid. This mass of suspended particulate abrasive has zero angle of repose, seeks its own level, while assuming the shape of the containing vessel.

BRIEF DESCRIPTION OF THE DRAWINGS

FIG. 2 is an enlarged top view of the system shown in FIG. 1 showing coated monofilament dental tape passing through the particulate abrasive coating chamber.

FIG. 3 is an expanded side view of a coated monofilament dental device showing a liquid base coating on both sides of the monofilament dental tape prior to entering the particulate abrasive coating chamber.

FIG. 4 is an expanded side view of coated monofilament dental tape showing particulate abrasive impinged onto the liquid base coating as the monofilament dental tape is passing through the particulate abrasive coating chamber.

FIG. 5 is an expanded side view of coated monofilament dental tape showing particulate abrasive adhered to the solidified base coating after the particulate abrasive overcoated, monofilament tape has been passed through a cooling zone (not shown).

FIG. 6 is a schematic side view of an alternative particulate abrasive overcoating system of the present invention suitable for overcoating coated monofilament devices.

FIG. 7 is a schematic side view of another alternative particulate overcoating system of the present invention suitable for overcoating wax-type coated monofilament devices, where the particulate used for overcoating is not detailed.

FIG. 8 is similar to FIG. 7, with the particulate used for overcoating shown in detail.

FIG. 9 is a schematic flow chart for particulate overcoating of coated monofilament dental floss.

DETAILED DESCRIPTION OF THE PREFERRED EMBODIMENTS

Referring to FIG. 1 which is a schematic side view of a particulate abrasive overcoating system comprising: particulate abrasive coating system, 1, consisting of fluidized bed means, 2, comprising: fluidized particulate abrasive, 3, membrane, 4, fluidizing air means, 5, stand pipe, 6, in communication with particulate abrasive nozzle means, 7, provided with pump means, 8, which contains nozzle air input means, 9, and pump cleaning means, 10.

Particulate abrasive coating system, 1, is provided with hinged access means, 11 and 15, and filter means, 12, particulate abrasive filling means, 13, and coated elastomeric, monofilament dental tape particulate abrasive coating zone, 14, and coated elastomeric monofilament dental tapes, 15. Filter means, 12, can be assisted by a vacuum cyclone means which capture all unused particulate, 3, overspray and recycles same. This is detailed in FIG. 1*a*.

Coated elastomeric monofilament dental tape, 15, with a liquid coating contained thereon, passes through particulate abrasive coating zone, 14, where particulate, 3, is introduced onto the liquid coating on tape, 15, from nozzle means, 7.

Referring to FIG. 1*a*, vacuum cyclone means, 60, replaces former filter means, 12, and is connected to the top of particulate coating system, 1, at juncture 61, via tubing means, 62. Vacuum cyclone means, 60, maintains a slight negative pressure within particulate coating system, 1, by drawing air and some dispersed particulate from coating system, 1, and introducing this air/particulate mixture into vacuum cyclone chamber, 63, where particulate, 3, is introduced into holding means, 64, and the remaining air substantially free from particulate, 3, passes through the top of chamber, 63, through tubing, 65, via motor, 67, into filter means, 66 and 66'. Alternatively, particulate, 3, is captured by collecting means, 68, with air regulator, 69, and returned to particulate coating system, 1, via tubing, 70.

Referring to FIG. 2, which is an enlarged top view of particulate coating system, 1. Elastomeric monofilament dental tape, 15, with liquid base coating, 16, thereon, passes through particulate abrasive coating zone, 14, where particulate abrasive, 3, from nozzle means, 7, is introduced via impinging onto liquid base coating, 16, which is substantive to tape, 15, as tape, 15, passes through particulate coating zone, 14.

Referring to FIG. 3, which is an expanded side view of monofilament tape, 15, showing base liquid coatings, 16 and 16', thereon before the tape, 15, passes into particulate abrasive coating zone, 14. The base coatings, 16 and 16', have been heated and are in a liquid state and substantive to both sides of monofilament tape, 15.

Referring to FIG. 4, which illustrates an expanded side view of coated monofilament tape, 15, showing base liquid coatings, 16 and 16' containing particulate abrasives, 3 and 3', imbedded in the liquid coatings, 16 and 16'.

Referring to FIG. 5, which is an expanded side view of coated monofilament dental tape, 15, showing base coatings, 16 and 16', that have been passed through a cooling zone (not shown) sufficient to be solidified with particulate abrasive, 3 and 3', firmly imbedded in the solidified liquid coatings, 16 and 16'.

Referring to FIG. 6, which is a schematic side view of an alternative particulate abrasive overcoating system, 20, for delivering a particulate abrasive, 21, from a vessel or fluidized-bed means, 30, to a conveying agent means, 22, with gear drive means, 23. The speed of conveying auger, 22, is controlled by motor driven gear means, 23, which is slaved to a surface speed controller, not shown, for monofilament tape, 24. As the monofilament tape, 24, moves faster, auger means, 22, speeds up and delivers more particulate abrasive, 21, to the surface of molten-coated monofilament tape, 24. This system then allows for the delivery of a constant density of particulate abrasive, 21, per square millimeter of monofilament tape, 24.

In the foregoing system, the particulate abrasive, 21, may be pumice of average particulate size of 37 microns which are fluidized with a porous plate of sintered polyethylene powder of 0.5 inch thickness. The plate has an average pore size of 20 microns. As the fluidized pumice is presented to auger means, 23, it is pulled down the shaft and presented to venturi means, 25. Control of the air flow in proportion to the speed allows uniform delivery of pumice to a surface of monofilament tape, 24, passing under the outlet of venturi means, 25. This arrangement allows delivery of uniform particle density with very low air speed, consistent with little perturbation of the tape traverse.

Referring to FIGS. 7 and 8, which are two separate schematic side views of another alternative particulate overcoating system, 40, for delivering particulates, 41, from a fluidized bed means, 42, to monofilament flosses, 43 and 43'.

Air chamber means, 44, introduces air under low pressure through distributor plate means, 45, which in turn fluidizes particulates, 41, in fluidized bed means, 46. Particulates, 41, are introduced from fluidized bed, 46, into particulate coating chamber, 47, by particulate metering means, 48. Particulate coating chamber, 47, is provided with venturi means, 49. Modulating particulate dispensing means, 50, is provided with high velocity, low volume air means (not shown) providing turbulence to fluidized particulate, 41, prior to said particulate imbedding coatings, 51 and 51', on the monofilament floss filaments, 43 and 43', respectively.

Particulate dispensing means, 50, enhances the uniformity of the particulate, 41, overcoating, 52 and 52', imbedded into coatings, 51 and 51', respectively.

Figure 8:
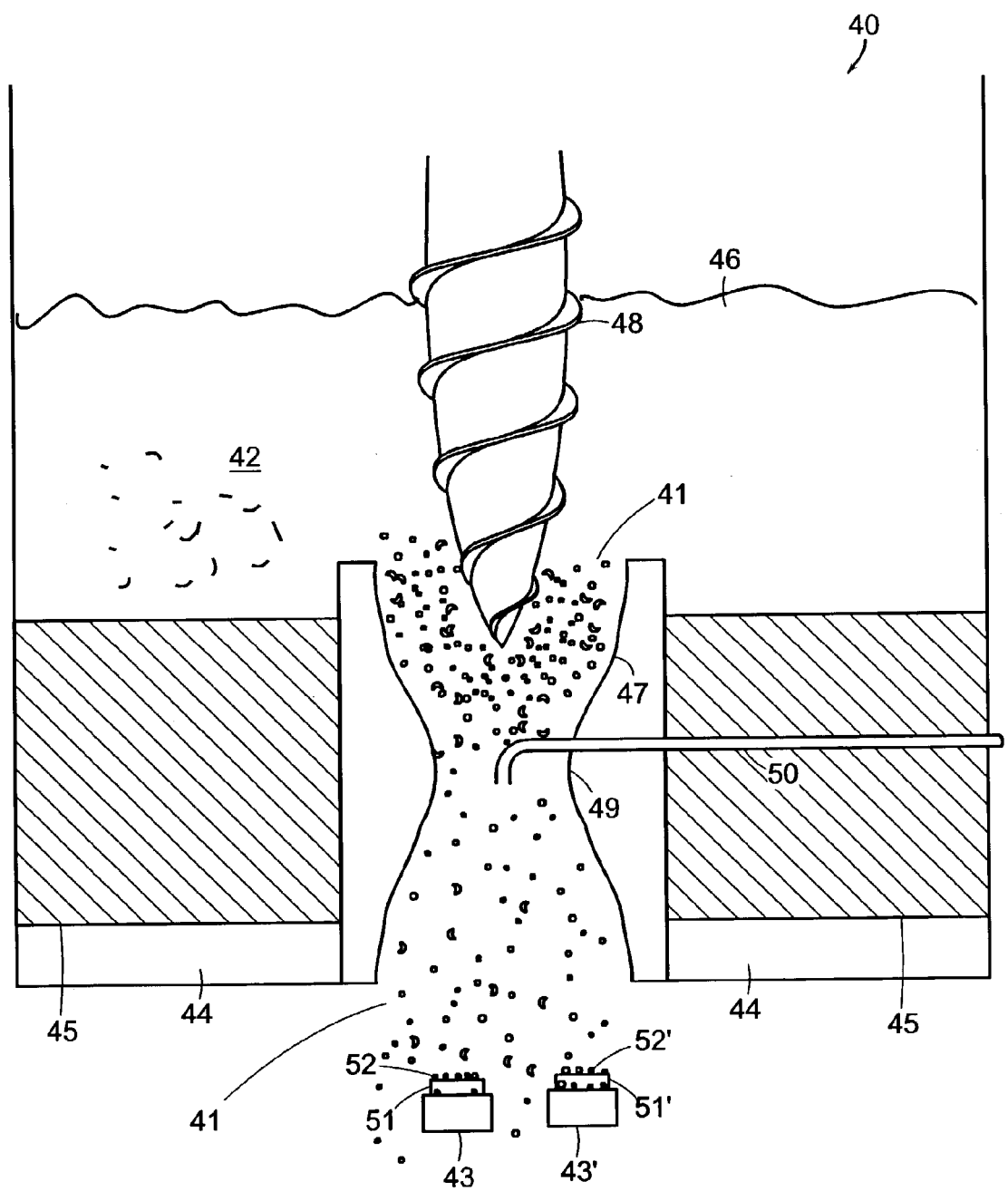

Referring to FIG. 8, generally the pressure in air chamber, 44, is between 4 and 8 psi. Distributor plate, 45, is preferably a porous polyethylene means that creates air bubbles required to fluidize particulates, 41, in fluidized bed, 42. The air pressure in fluidized bed, 42, is preferably in the 0.2 to 0.5 psi range. Particulate metering means, 48, can take many shapes other than that of the threaded means depicted. For example, metering means can be a plug or ram without threads that controls the flow of particulates, 41, from fluidized bed, 42, into particulate coating chamber, 47. Lowering metering means, 48, into particulate coating chamber, 47, as shown by dotted lines, 52, further restricts the flow of fluidized particulate, 41, through distance, 53. Thus, particulate metering means, 48, determines the quantity of fluidized particulate, 41, to enter particulate metering area, 47. This control in combination with modulated air flow through particulate dispersing means, 50, produces a substantially uniform density particulate on coating, 51, with imbedded particulates, 52, being dispersed substantially uniformly throughout coating, 51.

For a production system comprising up to 32 monofilament lines running side-by-side, the particulate overcoating system, 40, will be replicated in groups of 8, with two such groups covering the total of 32 lines running side-by-side.

Figure 9:
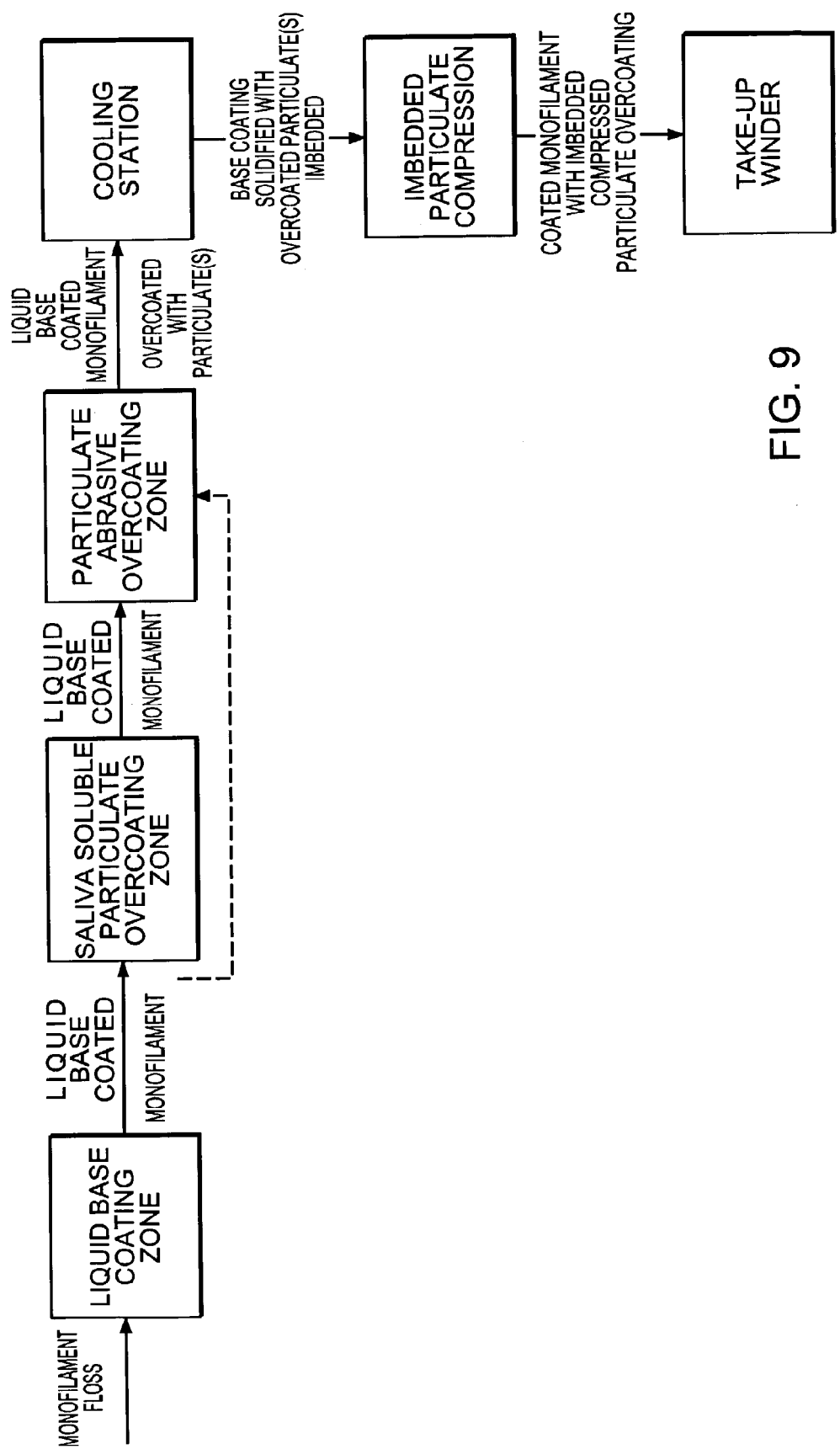

Referring to FIG. 9, which is a schematic flow chart for particulate overcoating of coated monofilament dental floss, monofilament floss is passed through liquid base coating zone where the base coating is applied. Particulate overcoating is applied by introducing the coated monofilament into one or two particulate overcoating zones, after which the particulate overcoated monofilament floss passes through a cooling zone, followed by passing the overcoated monofilament through a particulate compression means before being introduced to a take-up winder means.

The particulate abrasives of the present invention are applied to the coated monofilament dental tape base coatings as a solid material totally free from solvents.

Figure 1:
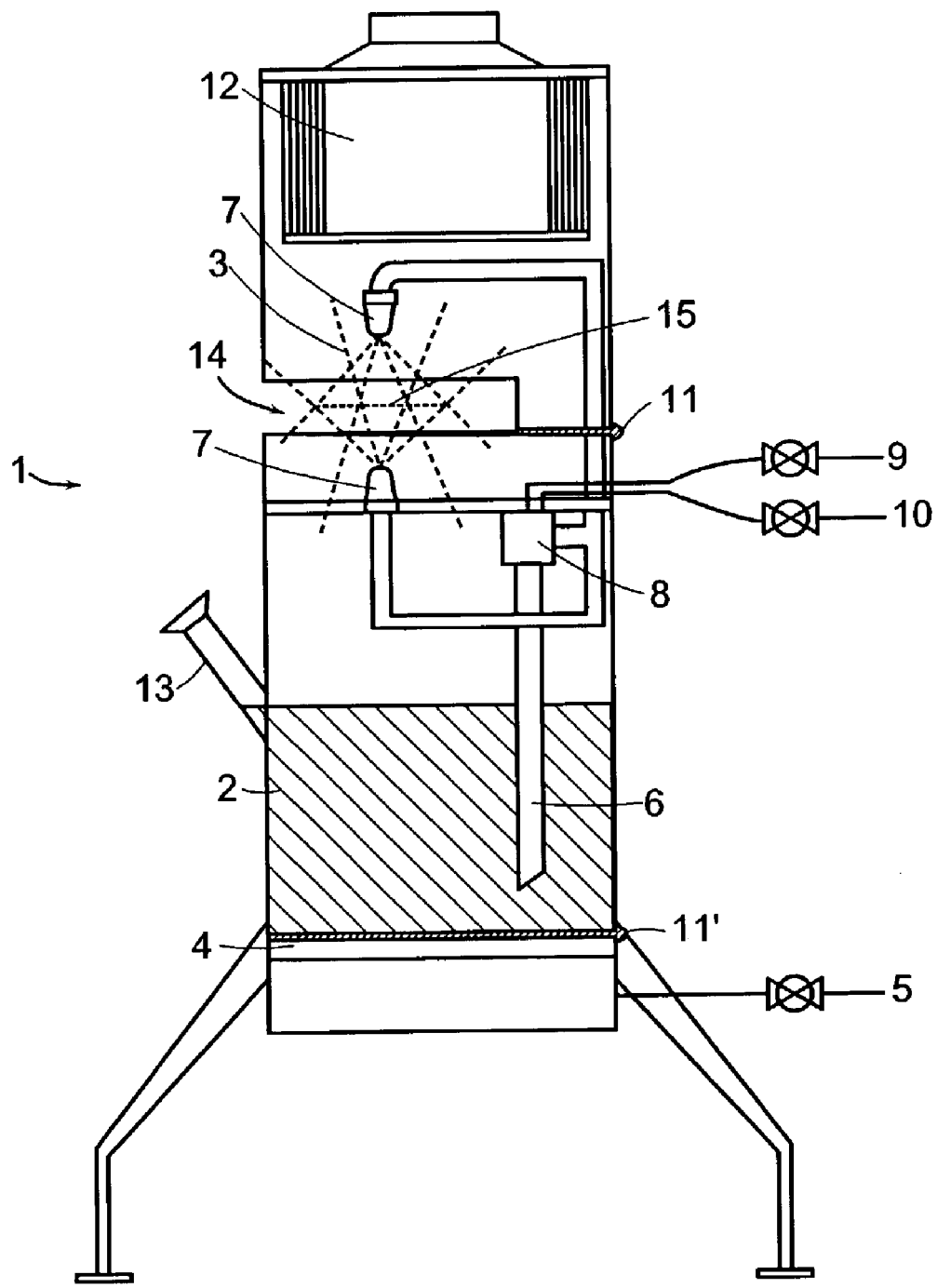
FIG. 1 is a schematic side view of a particulate abrasive overcoating system of the invention suitable for overcoating coated monofilament devices.
Figure 1A:
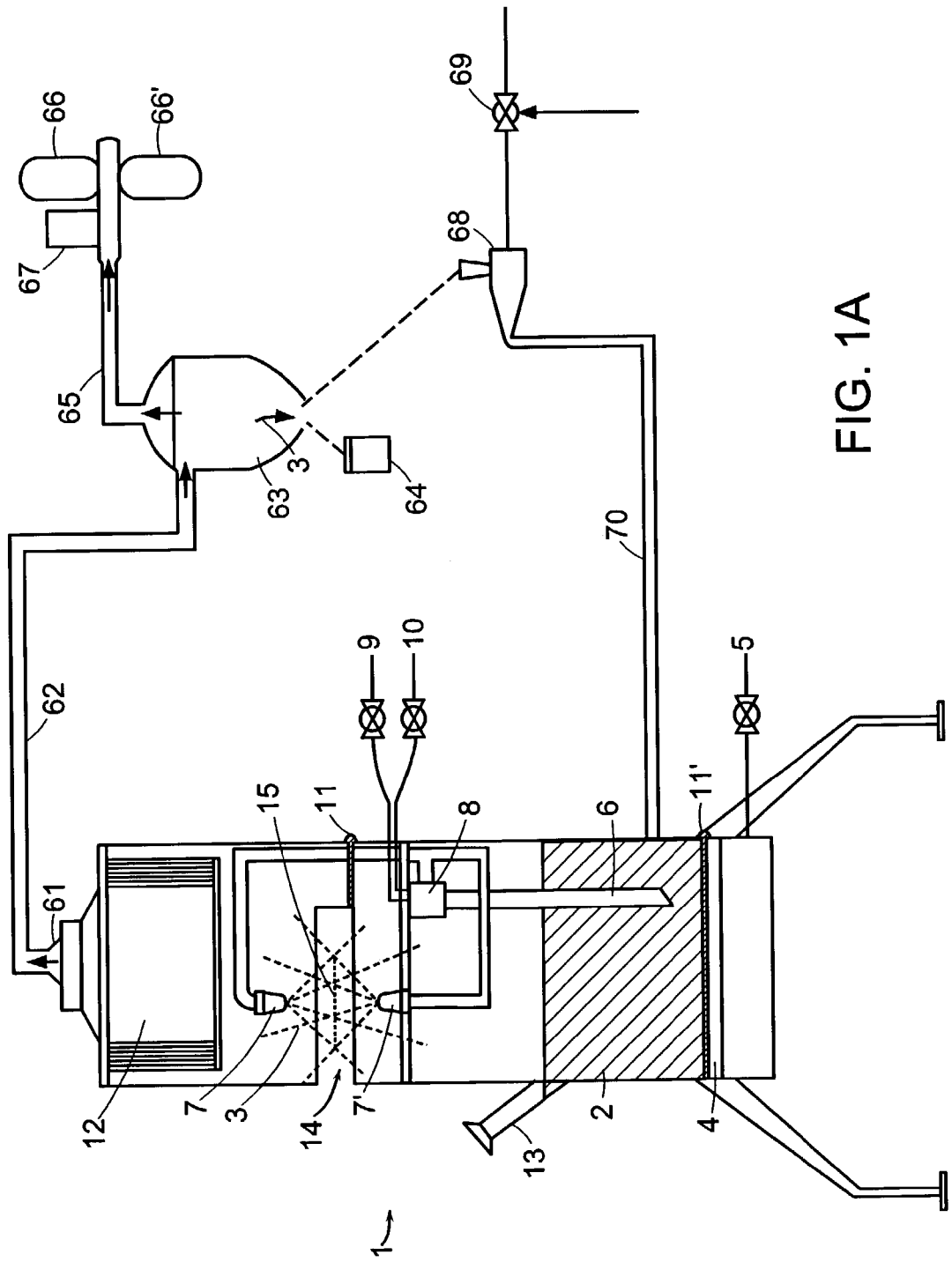
FIG. 1a is a schematic side view of a particulate overcoating system as shown in FIG. 1, with the filter means replaced by fitted with means to recover the particulate overspray that does not contact the monofilament during the overcoating operation.

A preferred method of applying the particulate abrasive overcoatings to the coated monofilament device is by means of an innovative fluidized bed system such as shown in FIG. 1.

Membrane means, 4, is used to maintain the particulate abrasive, 3, in a state of continued fluidization, i.e., fluidized bed, 2. Particulate abrasive, 3, from fluidized bed, 2, is introduced into nozzle means, 7, through stand pipe means, 6, via pump means, 8.

Figure 2:
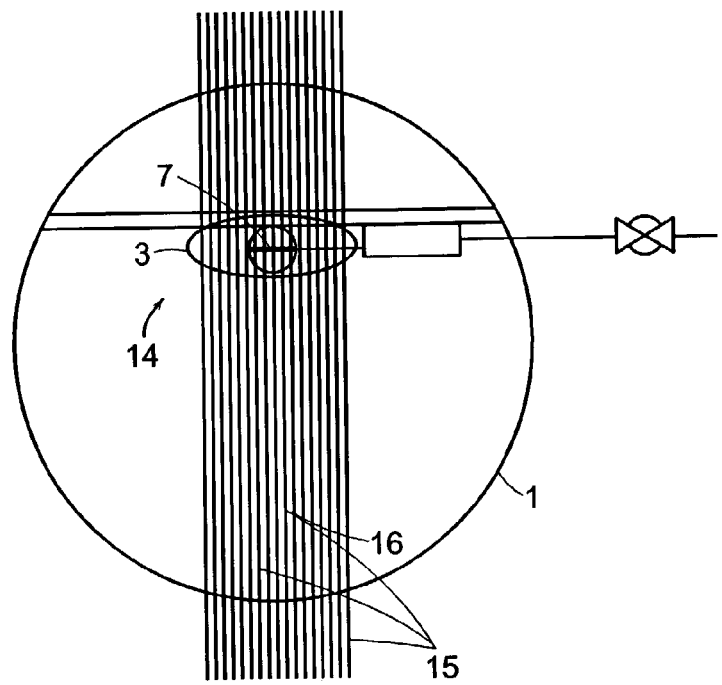
Figure 3:
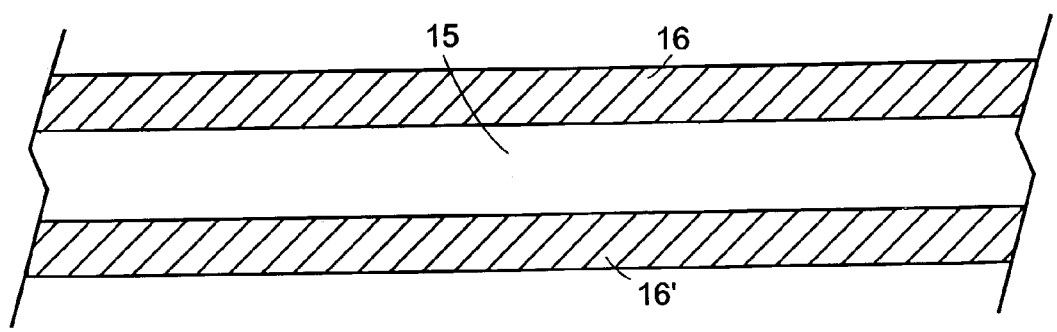
Figure 6:
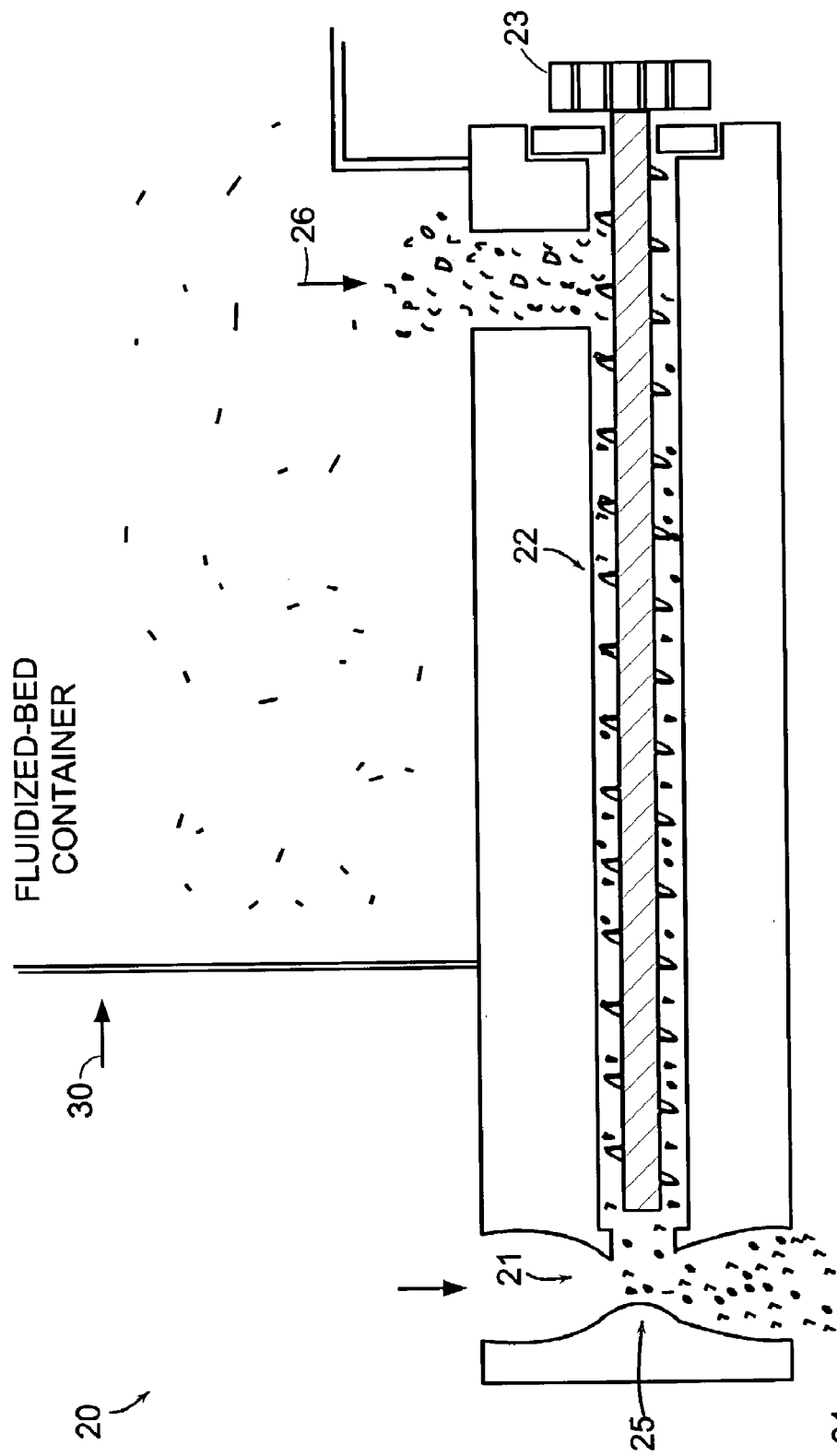
Figure 7:
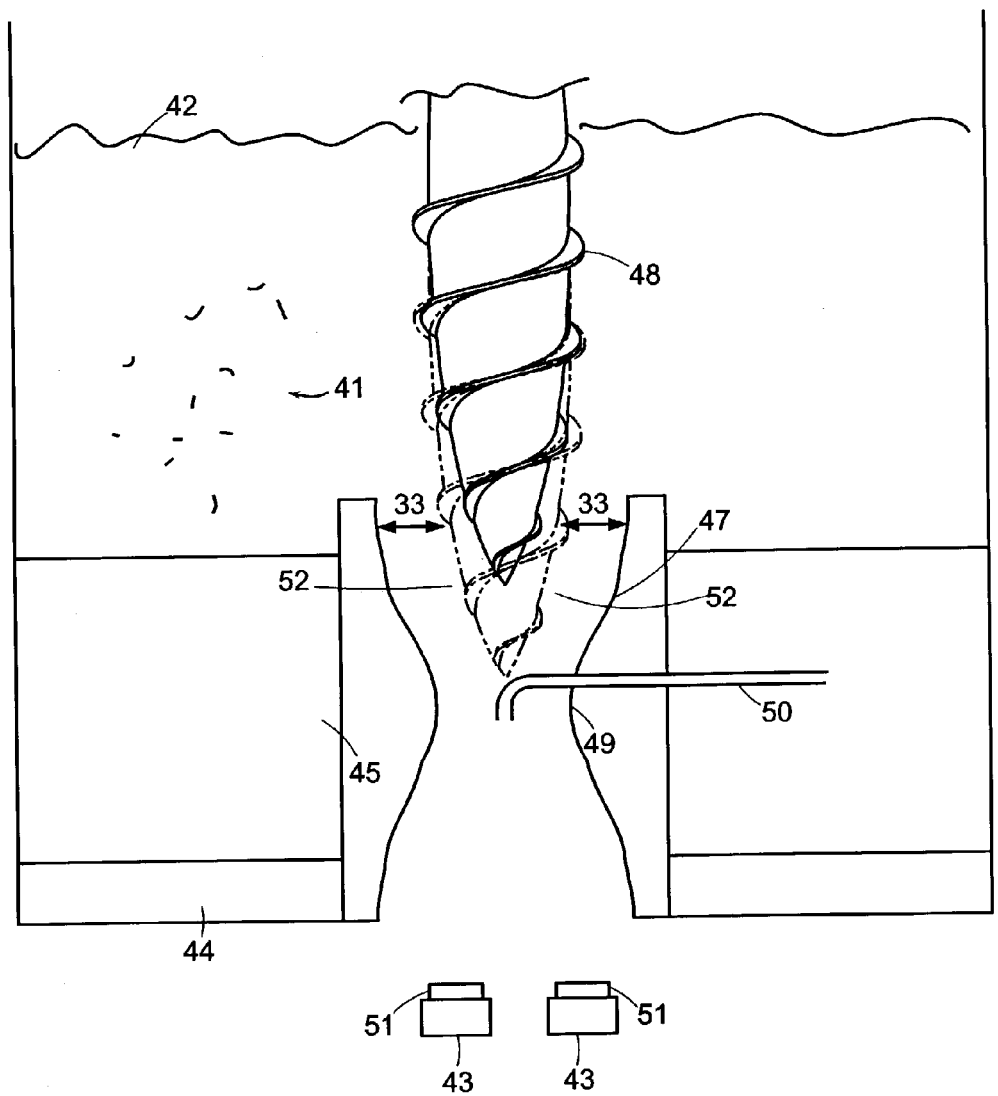

Referring to FIG. 2, coated monofilament dental tape, 15, passes through particulate abrasive coating zone, 14, and is coated on both sides with particulate abrasive, 3 and 3', as shown in FIGS. 4 and 5.

Adhesion of the particulate abrasive to the coated monofilament dental device is achieved by means of the hot, liquid base coating that is present on the monofilament device at the time the particulate abrasive, 3 and 3', impinges the tape coatings, 16 and 16'. See FIGS. 4 and 5.

That is, the particulate abrasive, 3, impinges onto liquid coatings, 16 and 16', which are substantive to monofilament device, 15, as the device passes through coating zone, 14, and particulate abrasives, 3 and 3', are trapped by and mechanically adheres to the hot, viscous base coating, 16 and 16', respectively, which is a viscous liquid generally at a temperature between about 48° C. and 110° C. with a viscosity between 10 and 10,000 cs. This is illustrated in FIGS. 4 and 5.

The particulate abrasive, overcoated, monofilament dental tape then proceeds through a cooling means (not shown), where the base coating, 16 and 16', cools and solidifies with the particulate abrasive, 3 and 3', adhered thereto, as illustrated in FIG. 5.

The innovative fluidized bed coating process of the present invention is most effective in delivering:

(1) particulate abrasive loads between about 2 and about 45 percent by weight of the device, (2) particulate abrasive overcoated monofilament devices with a perceived abrasive factor (PAF) between about 2 and 4, and (3) particulate abrasive, overcoated, monofilament devices with an Incidental Release Factor (IRF) value well above 80%.

It has been discovered that in order to produce a coated monofilament dental device with PAF values in the 3 to 4 range, it is necessary: (1) to produce particulate abrasive loads at between about 10 and 34 percent by weight of the device, (2) to restrict the average particle size of the particulate abrasive to between about 7 microns and about 200 microns, and (3) to restrict particle size distributions to from between about 5 microns and about 300 microns.

Dental particulate abrasives overcoated onto a standard coated monofilament dental tape and suitable for purposes of the present invention illustrated in Examples 1 through 7, are described in Table 1 below:

TABLE 1

"Dental" Particulate Abrasives

| Example # | Particulate Abrasive(s) | Avg. Particle Size (in microns) | Particle Size Distribution (in microns) | Particulate Abrasive Load as % by wt. of device | Projected Incidental Release Factor (IRF) in % | Projected Perceived Abrasive Factor (PAF) | Comments |
|---|---|---|---|---|---|---|---|
| 1 | pumice | 35 | 4–120 | 23 | 95 | 3.5 | Ideal professional product |
| 2 | silica | 10 | 2–18 | 10 | 98 | 1.5 | — |
| 3 | pumice & silica | 12 | 2–120 | 16 | 96 | 2.5 | Ideal for stain fighting |
| 4 | dicalcium phosphate dihydrate | 55 | 18–100 | 15 | 98 | 1.5 | Supports toothpaste positioning |
| 5 | alumina | 25 | 10–75 | 20 | 94 | 3.7 | — |
| 6 | calcium carbonate | 50 | 15–80 | 16 | 97 | 2.0 | — |

TABLE 1-continued

"Dental" Particulate Abrasives

| Example # | Particulate Abrasive(s) | Avg. Particle Size (in microns) | Particle Size Distribution (in microns) | Particulate Abrasive Load as % by wt. of device | Projected Incidental Release Factor (IRF) in % | Projected Perceived Abrasive Factor (PAF) | Comments |
|---|---|---|---|---|---|---|---|
| 7 | polyethylene | 20 | 8–40 | 12 | 98 | 1.5 | Supports soft abrasive positioning |

"Active" particulate abrasives overcoated onto a standard coated monofilament dental tape and suitable for purposes of the present invention are illustrated in Examples 8 through 12 in Table 2 below:

TABLE 2

"Active" Particulate Abrasives

| Example # | Particulate Abrasive(s) | Avg. Particle Size (in microns) | Particle Size Distribution (in microns) | Particulate Abrasive Load as % by wt. of device | Projected Incidental Release Factor (IRF) in % | Projected Perceived Abrasive Factor (PAF) | Comments |
|---|---|---|---|---|---|---|---|
| 8 | tricalcium phosphate & silica | 60 | 10–150 | 10 | 90 | 3.0 | Excellent tartar control product |
| 9 | tetrapotassium pyrophosphate & pumice | 65 | 20–175 | 12 | 90 | 2.5 | Tartar control prospect |
| 10 | tetra sodium pyrophosphate | 70 | 20–150 | 8 | 90 | 2.5 | Excellent tartar control product |
| 11 | sodium hexametaphosphate & pumice | 75 | 20–175 | 17 | 85 | 3.0 | Excellent whitening product |
| 12 | calcium pyrophosphate & silica | 9 | 4–35 | 20 | 98 | 2.0 | — |

Suitable particulate abrasives for the present invention can also contain active ingredients "dusted" thereon. For example, when antimicrobials such as cetylpyridinium chloride, triclosan, chlorhexidine, etc., can be dusted onto the particulate abrasives prior to overcoating the coated monofilament tape. During flossing, these antimicrobial containing particulate abrasives are released from the coated monofilament dental tapes and the dusted on antimicrobials release from the particulate abrasive and remain available interproximally and subgingivally to work with the monofilament dental tape during flossing as biofilms are being removed, disrupted and/or controlled.

The enhanced softness of the preferred elastomeric monofilament dental tapes suitable for use with the present invention is key to the tapes' consumer perception of gentleness, which is a distinct advantage over current commercial monofilament tapes and multifilament waxed flosses.

Wound bobbins of monofilament dental tapes suitable for overcoating with the particulate abrasive overcoatings of the present invention showed substantially lower Shore D hardness values than competitive tapes when tested with the Flexbar Portable Shore Hardness Tester Model Number 18877. See Table 3 below. This aspect of gentleness, of course, is primarily attributed to the substantive, saliva soluble, flake-free base coatings, such as described in Table 8, applied to the various monofilament tapes prior to overcoating.

TABLE 3

| Bobbin Type | Polymer Tape | Tape Coating | Shore D Hardness |
|---|---|---|---|
| Glide ® Floss - mint | PTFE | Wax | 36 |
| Glide ® Tape | PTFE | Wax | 36 |
| Oral-B ® Satin ® Tape - mint | Bicomponent | Wax | 29 |
| Fibaclean ™ unwaxed | PEBA | None | 37 |
| Fibaclean ™ noncrystalline coating | PEBA | Noncrystalline Non flaking | 27 |

Tables 4 through 7 below describe in detail monofilament tapes suitable for overcoating with the particulate abrasives of the present invention. The "UTILITY FACTORS": Gentleness Perception, Tape Flex-Twist Index and Hardness Shore D of these monofilament dental tapes when combined with various base coatings as described in Table 8, Examples 71 through 88 contribute to a consumer perception of gentleness. The particulate abrasive overcoatings added to these monofilament tapes imparts a perception of "working" to the perception of gentleness.

TABLE 4

Examples of Suitable Monofilament Dental Tapes

TAPE COMPOSITION

| Ex. No. | Thermoplastic Elastomer Type | Manufacturer | Trade Name | Grade | Silicone Process Aid (%) | TiO₂ (%) | Secondary Polymer added Type (%) | Other Add'n Type (%) |
|---|---|---|---|---|---|---|---|---|
| 13 | PEBA polyester amide | Atofina | PEBAX | 55/33 | 3.5 | 1.8 | PP - 4.7 | — |
| 14 | PEBA polyester amide | " | " | " | 3.5 | 1.8 | PP - 4.7 Adflex - 5 | — |
| 15 | PEBA polyester amide | " | " | " | 3.5 | 1.8 | PP - 9.7 | — |
| 16 | PEBA polyester amide | Atofina | PEBAX | 63/33 | 0 | 0 | 0 | — |
| 17 | PEBA polyester amide | " | " | " | 0 | 1.8 | PP - 1.2 | — |
| 18 | PEBA polyester amide | " | " | " | 3.5 | 1.8 | PP - 4.7 | — |
| 19 | PEBA polyester amide | " | " | " | 3.5 | 1.8 | PP - 4.7 Adflex - 5 | — |
| 20 | PEBA polyester amide | " | " | " | 3.5 | 1.8 | PP - 9.7 | — |
| 21 | PEBA polyester amide | " | " | " | 3.5 | 1.8 | PP - 4.7 Nylon 11–5 | — |
| 22 | TPE polyether ester | DuPont | Hytrel | 6359FG | 2.3 | 1.0 | 0 | Ca Stearate 0.1 |
| 23 | TPE polyether ester | " | " | " | 3.5 | 1.8 | PP - 4.7 | Ca Stearate 0.1 |
| 24 | TPE-E polyether ester | DSM | Arnitel | PM581 | 0 | 0 | 0 | — |
| 25 | TPE-E polyether ester | " | " | " | 0 | 1.8 | PP - 1.2 | — |
| 26 | TPE-E polyether ester | " | " | " | 3 | 0 | PBT - 5 | — |
| 27 | TPE-E polyether ester | " | " | " | 0 | 0 | PBT - 5 | — |
| 28 | TPE-E polyether ester | " | " | " | 0 | 1.8 | PP - 1.2 PBT - 5 | — |

| | PROCESSING CONDITIONS | | | PROPERTIES | | | DIMENSIONS | | UTILITY FACTORS | | |
|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit | Decitex | Width (mm) | Thick (mm) | Tape Gentleness Perception | Flex Twist Index | Hardness Shore D |
| 13 | 260 | 130 | 6.8:1 | 30 | 26 | 0 | 750 | 1.30 | 0.063 | 6 | 4 | 37 |
| 14 | 260 | 130 | 6.5:1 | 27 | 18 | 0 | 760 | 1.30 | 0.063 | 6 | 4 | 37 |
| 15 | 260 | 130 | 6.8:1 | 26 | 19 | 0 | 760 | 1.30 | 0.063 | 6 | 4 | 37 |
| 16 | 260 | 135 | 6:1 | 30 | 15 | 0 | 805 | 1.44 | 0.065 | 5.5 | 4 | 36 |
| 17 | 260 | 135 | 6.3:1 | 32.36 | 13 | 0 | 800 | 1.41 | 0.067 | 5.5 | 4 | 36 |
| 18 | 260 | 135 | 6.2:1 | 33.47 | 17 | 0 | 860 | 1.36 | 0.066 | 5.5 | 4 | 36 |
| 19 | 260 | 135 | 6.2:1 | 25.94 | 14 | 0 | 810 | 1.32 | 0.078 | 5.5 | 4 | 36 |
| 20 | 260 | 135 | 6.2:1 | 29.46 | 14 | 0 | 780 | 1.34 | 0.069 | 5.5 | 4 | 36 |
| 21 | 260 | 135 | 6.2:1 | 30.63 | 13 | 0 | 810 | 1.30 | 0.065 | 5.5 | 4 | 36 |
| 22 | 225 | 130 | 5:1 | 20 | 20 | 15 | 1400 | 1.70 | 0.070 | 7 | 3 | 33 |
| 23 | 225 | 140 | 5.7:1 | 24 | 14 | 10 | 1230 | 1.70 | 0.070 | 7 | 3 | 33 |
| 24 | 235 | 140 | 4.3:1 | 18 | 13 | 10 | 1500 | 1.63 | 0.084 | 7 | 3 | 33 |
| 25 | 240 | 115 | 4.3:1 | 19 | 14 | 5 | 1634 | 1.64 | 0.085 | 7 | 3 | 33 |
| 26 | 235 | 140 | 4.3:1 | 19 | 10 | 2 | 1580 | 1.68 | 0.079 | 7 | 3 | 33 |
| 27 | 235 | 140 | 4.3:1 | 18 | 12 | 3 | 1500 | 1.70 | 0.086 | 7 | 3 | 33 |
| 28 | 235 | 140 | 4.3:1 | 21 | 15 | 4 | 1575 | 1.77 | 0.083 | 7 | 3 | 33 |

TABLE 5

Examples of Suitable Monofilament Dental Tapes

TAPE COMPOSITION

| Ex. No. | Thermoplastic Elastomer Type | Manufacturer | Trade Name | Grade | Silicone Process Aid (%) | TiO$_2$ (%) | Secondary Polymer added Type (%) | Other Add'n Type (%) |
|---|---|---|---|---|---|---|---|---|
| 29 | TPE-E polyether ester | DSM | Arnitel | EM550 | 0 | 0 | 0 | — |
| 30 | TPE-E polyether ester | " | " | " | 0 | 1.8 | PP - 1.2 | — |
| 31 | TPE-E polyether ester | " | " | " | 0 | 1.8 | PP - 6.2 | — |
| 32 | TPE-E polyether ester | " | " | " | 0 | 0 | PBT - 5 | — |
| 33 | TPE-E polyester ester | OSM | Arnitel | EM630 | 0 | 0 | 0 | — |
| 34 | TPE-E polyether ester | " | " | " | 0 | 1.8 | PP - 1.2 | — |
| 35 | TPE-E polyether ester | " | " | " | 0 | 1.8 | PP - 1.2 Adflex - 5 | — |
| 36 | TPE-E polyether ester | " | " | " | 0 | 1.8 | PP - 6.2 | — |
| 37 | TPE-E polyether ester | " | " | " | 0 | 0 | PBT - 5 | — |
| 38 | TPE-E polyester ester | DSM | Arnitel | UM552 | 0 | 0 | 0 | — |
| 39 | TPE-E polyether ester | " | " | " | 0 | 0 | 0 | Ca Stearate 0.1 |
| 40 | TPE-E polyether ester | " | " | " | 0 | 1.8 | PP - 1.2 | — |
| 41 | TPE-E polyether ester | " | " | " | 0 | 0 | Adflex - 5 | — |
| 42 | TPE-E polyether ester | " | " | " | 0 | 1.5 | PP - 1.2 PBT - 5 | Ca Stearate 0.1 |
| 43 | TPE-E polyether ester | " | " | " | 0 | 0 | PBT - 5 | Ca Stearate 0.1 |
| 44 | EPDM TPV | Monteil | Adflex | Q100F | 0 | 0 | PP - 20 | — |
| 45 | EPDM TPV | " | " | " | 3.5 | 1.8 | PP - 24.7 | — |
| 46 | EPDM TPV | " | " | " | 0 | 3 | PP - 30 | — |
| 47 | EPDM TPV | " | " | " | 0 | 3 | PP - 34.7 | — |
| 48 | EPDM TPV | " | " | " | 0 | 3 | PP - 40 | — |

| | PROCESSING CONDITIONS | | | PROPERTIES | | | | | UTILITY FACTORS | | |
|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit | Decitex | Width (mm) | Thick (mm) | Tape Flex Gentleness Perception | Twist Index | Hardness Shore D |
| 29 | 240 | 140 | 4.3:1 | 23 | 25 | 7 | 1800 | 1.95 | 0.096 | 7 | 3 | 33 |
| 30 | 240 | 115 | 6:1 | 27 | 11 | 5 | 1050 | 1.47 | 0.071 | 7 | 3 | 33 |
| 31 | 240 | 140 | 5.6:1 | 26 | 17 | 5 | 1216 | 1.45 | 0.071 | 7 | 3 | 33 |
| 32 | 240 | 145 | 5.9:1 | 28 | 145 | 5 | 1220 | 1.55 | 0.074 | 7 | 3 | 33 |
| 33 | 235 | 150 | 4.5:1 | 18 | 12 | 4 | 1090 | 1.44 | 0.067 | 7 | 3 | 33 |
| 34 | 235 | 150 | 4.7:1 | 17 | 11 | 4 | 1130 | 1.50 | 0.068 | 7 | 3 | 33 |
| 35 | 235 | 150 | 4.6:1 | 18 | 10 | 7 | 961 | 1.35 | 0.065 | 7 | 3 | 33 |
| 36 | 235 | 150 | 4.6:1 | 14 | 30 | 10 | 965 | 1.24 | 0.073 | 7 | 3 | 33 |
| 37 | 235 | 150 | 4.6:1 | 20 | 12 | 5 | 1018 | 1.39 | 0.069 | 7 | 3 | 33 |
| 38 | 240 | 150 | 6.6:1 | 32 | 12 | 8 | 1300 | 1.49 | 0.070 | 7.5 | 3.5 | 31 |
| 39 | 230 | 150 | 5.6:1 | 26 | 15 | 8 | 1090 | 1.40 | 0.070 | 7.5 | 3.5 | 31 |
| 40 | 240 | 150 | 6.3:1 | 29 | 16 | 8 | 1150 | 1.46 | 0.070 | 7.5 | 3.5 | 31 |
| 41 | 230 | 140 | 5.6:1 | 30 | 16 | 10 | 1233 | 1.48 | 0.069 | 7.5 | 3.5 | 31 |
| 42 | 230 | 145 | 5.7:1 | 22 | 19 | 10 | 1108 | 1.53 | 0.067 | 7.5 | 3.5 | 31 |
| 43 | 230 | 245 | 5.3:1 | 24 | 14 | 8 | 1143 | 1.48 | 0.064 | 7.5 | 3.5 | 31 |
| 44 | 240 | 130 | 4.5:1 | 26 | 20 | 0 | 910 | 1.60 | 0.064 | 5.5 | NT | NT |
| 45 | 240 | 130 | 4.5:1 | 25 | 24 | 0 | 940 | 1.59 | 0.064 | 5.5 | NT | NT |
| 46 | 240 | 130 | 4.7:1 | 28 | 20 | 0 | 870 | 1.58 | 0.064 | 5.5 | NT | NT |

TABLE 5-continued

Examples of Suitable Monofilament Dental Tapes

| 47 | 240 | 130 | 4.7:1 | 27 | 23 | 0 | 880 | 1.58 | 0.060 | 5.5 | NT | NT |
| 48 | 240 | 130 | 4.7:1 | 35 | 18 | 0 | 720 | 1.44 | 0.063 | 5 | NT | NT |

TABLE 6

Examples of Suitable Monofilament Dental Tapes

TAPE COMPOSITION

| Ex. No. | Thermoplastic Elastomer Type | Manufacturer | Trade Name | Grade | Silicone Process Aid (%) | $TiO_2$ (%) | Secondary Polymer added Type (%) | Other Add'n Type (%) |
|---|---|---|---|---|---|---|---|---|
| 49 | PEBA polyester amide | Atofina | PEBAX | 55133 | 0 | 1.8 | PP - 1.2 | — |
| 50 | PEBA polyester amide | " | " | " | 3.5 | 1.8 | PP - 4.7 EMA - 3 | — |
| 51 | PEBA polyester amide | " | " | " | 3.5 | 1.8 | PP - 4.7 | — |
| 52 | PEBA | Atofina | PEBAX | 63/33 | 3.5 | 1.8 | PP - 4.7 EMA - 3 | — |
| 53 | " | " | " | " | 0 | 0 | Nylon 11 - 5 | PDVF - 3 |
| 54 | TPE - E polyether ester | DSM | Arnitel | PM581 | 3 | 0 | 0 | — |
| 55 | TPE - E polyether ester | DSM | Arnitel | EM550 | 3 | 0 | 0 | — |
| 56 | TPE - E polyether ester | " | " | " | 3 | 1.8 | PP - 1.2 EMA - 3 | — |
| 57 | TPE - E polyether ester | DSM | Arnitel | UM552 | 3 | 1.8 | PP - 1.2 | — |

| | PROCESSING CONDITIONS | | | PROPERTIES | | | | | | UTILITY FACTORS | | |
|---|---|---|---|---|---|---|---|---|---|---|---|---|
| Ex. No. | Melt Temp °C. | Draw Temp °C. | Draw Ratio | Break Strength in Newtons | Elongation to Break (%) | Elastic Limit | Decitex | DIMENSIONS Width (mm) | Thick (mm) | Tape Gentleness Perception | Flex Twist Index | Hardness Shore D |
| 49 | 260 | 130 | 6.8:1 | 28 | 24 | 0 | 775 | 1.30 | 0.063 | 6 | 4 | 37 |
| 50 | 260 | 130 | 7:1 | 28 | 30 | 3 | 750 | 1.30 | 0.063 | 8 | 4 | 37 |
| 51 | 260 | 130 | 6.8:1 | 29 | 24 | 0 | 800 | 1.35 | 0.070 | 6 | 4 | 37 |
| 52 | 260 | 135 | 6.5:1 | 31 | 20 | 3 | 800 | 1.40 | 0.065 | 5.5 | 4 | 36 |
| 53 | 260 | 135 | 6.2:1 | 28 | 14 | 0 | 800 | 1.30 | 0.065 | 5.5 | 4 | 36 |
| 54 | 235 | 140 | 5:1 | 22 | 16 | 7 | 1400 | 1.60 | 0.079 | 7 | 3 | 33 |
| 55 | 240 | 140 | 6:1 | 25 | 20 | 7 | 800 | 1.30 | 0.060 | 7 | 3 | 33 |
| 56 | 240 | 140 | 6:1 | 27 | 15 | 5 | 850 | 1.35 | 0.065 | 7 | 3 | 33 |
| 57 | 240 | 150 | 6:1 | 27 | 17 | 10 | 1100 | 1.47 | 0.069 | 7.5 | 3 | 33 |

TABLE 7

Examples of Suitable Monofilament Dental Tapes

TAPE COMPOSITION

| Ex. No. | Thermoplastic Elastomer Type | Manufacturer | Trade Name | Grade | Silicone Process Aid (%) | $TiO_2$ (%) | Secondary Polymer added Type (%) | Other Add'n Type (%) |
|---|---|---|---|---|---|---|---|---|
| 58 | Styrenics SEBS | Alphagary | Evoprene | G978 | 0 | 1.8 | PP - 1.2 | — |
| 59 | " | " | " | " | 3 | 1.8 | PP - 1.2 | — |
| 60 | " | " | " | " | 0 | 1.8 | PP - 1.2 EMA - 3 | — |
| 61 | " | " | " | " | 3.5 | 1.8 | PP - 9.7 | — |
| 62 | " | " | " | " | 3.5 | 1.8 | PP - 9.7 PS - 5 | — |
| 63 | TPU 90 AEN | Dow | Pelethane | 2103 | 0 | 1.8 | PP - 1.2 | — |

TABLE 7-continued

Examples of Suitable Monofilament Dental Tapes

| | | | | | | | | |
|---|---|---|---|---|---|---|---|---|
| 64 | " | " | " | " | 3 | 1.8 | PP - 1.2 | — |
| 65 | " | " | " | " | 0 | 1.8 | PP - 1.2 EMA - 3 | — |
| 66 | " | " | " | " | 3.5 | 1.8 | PP - 9.7 | — |
| 67 | TPV | DSM | Sarlink | 4149D | 0 | 1.8 | PP - 1.2 | — |
| 68 | " | " | " | " | 3 | 1.8 | PP - 1.2 | — |
| 69 | " | " | " | " | 0 | 1.8 | PP - 1.2 EMA - 3 | — |
| 70 | " | " | " | " | 3 | 1.8 | PP - 6.2 | — |

| | PROCESSING CONDITIONS | | | PROPERTIES | | | UTILITY FACTORS | | | | |
|---|---|---|---|---|---|---|---|---|---|---|---|
| | | | | Break Strength | Elongation to | | | | | Tape Flex | |
| | Melt | Draw | | in | Break | Elastic | | Width | Thick | Gentleness | Twist Hardness |
| Ex. No. | Temp °C. | Temp °C. | Draw Ratio | Newtons | (%) | Limit | Decitex | (mm) | (mm) | Perception | Index Shore D |
| 58 | 200 | 100 | 7:1 | 19 | 30 | 10 | 1100 | 1.30 | 0.060 | 6 | 4 37 |
| 59 | 200 | 100 | 7:1 | 20 | 35 | 12 | 1100 | 1.30 | 0.060 | 6 | 4 37 |
| 60 | 200 | 100 | 7.2:1 | 17 | 32 | 12 | 1100 | 1.30 | 0.060 | 6 | 4 37 |
| 61 | 200 | 100 | 7:1 | 14 | 20 | 7 | 1100 | 1.30 | 0.060 | 8 | 4 37 |
| 62 | 200 | 100 | 7:1 | 22 | 28 | 8 | 1100 | 1.30 | 0.060 | 6 | 4 37 |
| 63 | 230 | 120 | 7:1 | 32 | 15 | 5 | 1200 | 1.40 | 0.068 | 7 | 3 33 |
| 64 | 230 | 120 | 6:1 | 30 | 17 | 6 | 1200 | 1.40 | 0.068 | 7 | 3 33 |
| 65 | 230 | 120 | 6:1 | 26 | 16 | 6 | 1200 | 1.40 | 0.068 | 7 | 3 33 |
| 66 | 230 | 120 | 5:1 | 22 | 10 | 2 | 1300 | 1.45 | 0.070 | 7 | 3 33 |
| 67 | 220 | 105 | 4.5:1 | 20 | 20 | 5 | 1400 | 1.45 | 0.072 | 6 | 4 37 |
| 68 | 220 | 105 | 5:1 | 22 | 35 | 7 | 1300 | 1.40 | 0.070 | 6 | 4 37 |
| 69 | 220 | 105 | 4.8:1 | 19 | 20 | 5 | 1350 | 1.48 | 0.075 | 6 | 4 37 |
| 70 | 220 | 105 | 4.2:1 | 15 | 20 | 5 | 1450 | 1.48 | 0.075 | 6 | 4 37 |

Suitable crystal-free, substantially flake-free, base coatings for various monofilament dental tapes are described in Examples 71 through 88 in Table 8 below:

TABLE 8

Suitable Crystal-Free, Flake-Free Base Coatings for Monofilament Dental Tapes

| | EXAMPLE | | | | | | | | | | | | | | | | | |
|---|---|---|---|---|---|---|---|---|---|---|---|---|---|---|---|---|---|---|
| Ingredient | 71 | 72 | 73 | 74 | 75 | 76 | 77 | 78 | 79 | 80 | 81 | 82 | 83 | 84 | 85 | 86 | 87 | 88 |
| Ultramulsion 10–2.5 | 57.1 | 54.8 | 52.3 | 50.8 | 50.8 | 50.8 | 58.8 | 60.8 | | 60.1 | 55.1 | 51.1 | 60.1 | | 61.1 | 61.1 | 53.1 | 57.1 |
| POLOXAMER 407 | | | | | | | | | 60.1 | | | | | 60.1 | | | | |
| Emsorb 2726 | 12.5 | 7.5 | 12.5 | 9 | 5 | 3 | 3 | 0 | 3 | 3 | 3 | 3 | 3 | 3 | 4 | 3 | 3 | 3 |
| Stearyl Alcohol | 9.2 | 10.5 | 8 | 7 | 11 | 13 | 15 | 16 | 15 | 15 | 15 | 15 | 15 | 15 | 10 | 8 | 15 | 15 |
| Insoluble Saccharin | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 | 1.8 |
| Propyl gallate | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Spicemint Flavor | 4 | 4 | 4 | 4 | 4 | 4 | 4 | 4 | 5 | 5 | 5 | 5 | 5 | 5 | 5 | 5 | 5 | 5 |
| Vanilla Mint Flavor | 4 | 4 | 4 | 4 | 4 | 4 | 4 | 4 | 5 | 5 | 5 | 5 | 5 | 5 | 5 | 5 | 5 | 5 |
| Tetrasodiumpyro-phosphate | 8 | 14 | 14 | 10 | 10 | 10 | 10 | 10 | 10 | | 10 | 14 | 4 | | 6 | 6 | 10 | 6 |
| Dicalcium phosphate | | | | | | | | | | 10 | | | | | | | | |
| Microcrystalline Wax ML 445 | | | | 10 | 10 | 10 | 0 | 0 | 0 | 0 | 5 | 5 | | 0 | 7 | 10 | 7 | 7 |
| Triclosan | 3.3 | 3.3 | 3.3 | 3.3 | 3.3 | 3.3 | 3.3 | 3.3 | | | | | | | | | | |
| PEG 8000 | | | | | | | | | | | | | | | 11 | 6 | | |
| Need heat to wind | y | n | y | y | n | y | y | y | y | y | y | y | y | y | y | y | y | y |
| Bobbin tack (1 = poor, 5 = good) Flake resistance | 1 | | 5 | 5 | 3 | 4 | | 4 | 3 | 2 | 4 | 3 | 3 | 3 | 4 | 3 | 4 | 4 |
| Feels sticky (1 = no, 5 = very) | | | 5 | 4 | 4 | 2 | 1 | 2 | 2 | 3 | 3 | 3 | 1 | | 4 | 3 | 4 | 4 |

TABLE 8-continued

Suitable Crystal-Free, Flake-Free Base Coatings for Monofilament Dental Tapes

| | EXAMPLE | | | | | | | | | | | | | | | | | |
|---|---|---|---|---|---|---|---|---|---|---|---|---|---|---|---|---|---|---|
| Ingredient | 71 | 72 | 73 | 74 | 75 | 76 | 77 | 78 | 79 | 80 | 81 | 82 | 83 | 84 | 85 | 86 | 87 | 88 |
| Load of two samples | 29/19 | Na | Na | 43/50 | 28/11 | 53/39 | 58/43 | 33/20 | 51/40 | 33 | 46/53 | 40/39 | 38/38 | 50/37 | 48 | 45 | 38/39 | 43/39 |
| Release Value | 98 | 97 | 100 | 96 | 100 | 99 | 100 | 100 | 96 | 99 | 98 | 100 | 97 | 99 | 100 | 96 | 100 | 100 |

TABLE 9

Coated Monofilament Dental Tapes with an Overcoating of Particulate Abrasive

| Example No. | Monofilament Dental Tape Composition per example # | Base Coating (mg/yd) | Particulate Abrasive Overcoating (mg/yd) | Incidental Release Factor (IRF) (in %) | Perceived Abrasive Factor (PAF) | Comments |
|---|---|---|---|---|---|---|
| 89 | Example 13 (680) | 45 | pumice (20) | 95 | 3.5 | Suitable for professional use only product |
| 90 | Example 14 (730) | 47 | granular DCP (14) | 90 | 2.0 | Tartar control product |
| 91 | Example 13 (745) | 52 | alumina DCP (22) | 87 | 3.7 | Suitable for whitening/stain removal product |

TABLE 10

Wax Coated Monofilament Dental Tape Overcoated with Particulate Abrasive and Saliva Soluble Particulate

| | | | OVERCOATINGS | | | |
|---|---|---|---|---|---|---|
| Ex. No. | Monofilament Dental Tape Composition per Example No. | Wax Base Coating Type & Load (mg/yd) | Particulate Abrasive Type & Load (in mg/yd) | Projected PAF | Projected IRF | Saliva Soluble Particulate Type & Load (in mg/yd) | Impact of Saliva Soluble Particulate |
| 92 | Example 13 | microcrystalline wax (33) | pumice (21) | 3.4 | 96 | PEG 3350/flavor (14) | — |
| 93 | Example 14 | microcrystalline wax (33) | pumice (14) | 3.2 | 98 | PEG 3350/flavor (18) | — |
| 94 | Example 13 | microcrystalline wax (33) | silica (16) | 2.8 | 97 | PEG 3350/flavor (12) | — |
| 95 | Example 14 | bees wax (27) | pumice (22) | 3.5 | 92 | PEG 3350/flavor (14) | — |
| 96 | Example 13 | bees wax (27) | pumice (14) | 3.0 | 96 | PEG 3350/flavor (17) | — |

TABLE 11

Suitable Wax Coatings for Various Monofilament Dental Tapes

| Ex. No. | Monofilament Tape Composition per Example No. | Wax Base Coating Type (mg/yd) | Imbedded Particulate Abrasive-Type (mg/yd) | Projected IRF (in %) | Projected PAF (in %) | Estimated % of total particulate abrasive surface area imbedded into wax coating |
|---|---|---|---|---|---|---|
| 97 | Example 13 | microcrystalline wax (28) | pumice (20) | 92 | 3.6 | 17 to 24 |

TABLE 11-continued

Suitable Wax Coatings for Various Monofilament Dental Tapes

| Ex. No. | Monofilament Tape Composition per Example No. | Wax Base Coating Type (mg/yd) | Imbedded Particulate Abrasive-Type (mg/yd) | Projected IRF (in %) | Projected PAF (in %) | Estimated % of total particulate abrasive surface area imbedded into wax coating |
|---|---|---|---|---|---|---|
| 98 | Example 13 | microcrystalline wax (34) | pumice (12) | 98 | 3.2 | 13 to 16 |
| 99 | Example 14 | microcrystalline wax (34) | pumice (16) | 96 | 3.4 | 15 to 18 |
| 100 | Example 14 | microcrystalline wax (34) | Silica (15) | 98 | 2.8 | 19 to 26 |
| 101 | Example 13 | microcrystalline wax (34) | Silica (9) | 99 | 2.5 | 15 to 18 |
| 102 | Example 14 | Bees wax (24) | Pumice (20) | 94 | 3.5 | 16 to 25 |
| 103 | Example 13 | Bees wax (24) | Pumice (11) | 97 | 3.1 | 12 to 16 |
| 104 | Example 14 | Bees wax (24) | Silica (16) | 98 | 2.5 | 18 to 20 |
| 105 | Example 13 | PEG 3350 (30) | Pumice (21) | 90 | 3.7 | 18 to 26 |
| 106 | Example 13 | PEG 3350 (30) | Pumice (13) | 95 | 3.2 | 13 to 18 |
| 107 | Example 14 | PEG 3350 (30) | Pumice (9) | 98 | 2.9 | 10 to 13 |
| 108 | Example 14 | Bees wax (27) | Pumice (18) | 94 | 3.6 | 16 to 23 |

In addition to various types of fluidized beds, the particulate abrasive overcoatings can be introduced onto the coated monofilament dental tapes by several other means for impinging particulate abrasives onto coated tapes. These include various powder coating processes including fluidized bed, plastic frame-spraying, electrostatic spraying and sonic spraying. In the latter, sound waves are used to suspend the particulate abrasives. Some of these other particulate abrasive overcoating processes are described in U.S. Pat. Nos. 6,037,019; 3,848,363; 3,892,908; 4,024,295; 4,612,242; 5,163,975; 5,232,775; 5,273,782; 55,389,434; 5,658,510; 2,640,002; 3,093,501; 2,689,808; 2,640,001 and 5,194,297, which are incorporated herein by reference.

Particularly preferred particulate abrasive overcoating means include various Nordson® automatic powder coating systems such as the Nordson® Tribomatic II powder coating system, which includes various Nordson® powder pumps, as well as ITW Genca Powder coating systems including their Easysystem™ and Electrostatic Equipment Co's 7R FLEXICOAT® system.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. A coated monofilament dental device comprising a base coating applied over the device and an overcoating comprising a biofilm responsive particulate abrasive applied over the base coating, wherein said base coating is saliva soluble and said biofilm responsive particulate abrasive overcoating is saliva insoluble;

wherein said particulate abrasive coating comprises from between about 2 and about 45 percent by weight of said device; and wherein both the base coating and the overcoating are released from the substrate and from one another during use.

2. Monofilament dental devices coated with a saliva soluble, crystal-free, base coating;

wherein said coating has a biofllm responsive, particulate abrasive overcoating imbedded thereon, and wherein the particulate abrasive overcoating separates from the released base coating during use.

3. A monofilament dental device of claim 2, wherein said base coating comprises an emulsion.

4. A monofilament dental device of claim 2, wherein said particulate abrasive overcoating is a solvent-free solid.

5. A monofilament dental device of claim 2, wherein said particulate abrasive comprises active particulates.

6. A monofilament dental device of claim 2, wherein said particulate abrasive contains dusted thereon active ingredients.

7. A monofilarnent dental device of claim 2, wherein said monofilament material is selected from the group consisting of PTFE, polyethylene, polypropylene, elastomeric substrates and combinations thereof.

8. A monofilament dental device of claim 2, wherein said particulate abrasive is selected from the group consisting of organic, inorganic, dental and active abrasives and mixtures thereof.

9. A monofilament dental device of claim 2, wherein said particulate abrasive is saliva soluble and selected from the group consisting of emulsion particulates, crystal-free particulates and mixtures thereof.

10. A monofilament dental device of claim 2, wherein said particulate abrasive overcoating comprises from between about 2 and about 45 percent by weight of said coated substrate.

11. A monofilament dental device of claim 2, wherein said particulate abrasive overcoating has an Incidental Release Factor (IRF) of at least about 85 percent by weight.

12. A monofilanient dental device of claim 2, wherein said biofilm-responsive, particulate abrasive overcoating has an average particle size from between about 7 and 200 microns.

13. A monofilament dental device of claim 2, wherein said biofilm-responsive, particulate abrasive overcoating has a particle size distribution from between about 5 and 300 microns.

14. A monofliament dental device of claim 2, wherein said particulate abrasive overcoating also contains additional solid particulates selected from the group consisting of water soluble waxes, water soluble nonionic surfactants, emulsions of nonionic surfactants and polydimethylsiloxanes, and mixtures thereof.

15. A monofilament dental device of claim 14, wherein said dental device comprises polyethylene.

16. A monofilament dental device of claim 14, wherein said dental device comprises PTFE.

17. A monofilament dental device of claim 2, wherein said base coating contains a releasable antimicrobial.

18. A monofilament dental device of claim 2, wherein said biofilm-responsive particulate abrasive overcoating is a dental abrasive selected from the group consisting of silica, pumice, alumina, calcium carbonate, dicalcium phosphate dihydrate and mixtures thereof.

19. A monofilament dental device of claim 2, wherein said biofilm-responsive particulate abrasive overcoating is an active abrasive selected from the group consisting of whitening, tartar control, stain fighting, hypersensitivity treatment abrasives and mixtures thereof.

20. A dental device comprising:
 a monofilament substrate;
 coated with a saliva soluble base coating; and
 overcoated with a biofilm-responsive particulate abrasive imbedded thereon; and
 wherein both the base coating and the overcoating are released from the substrate and from one another during use.

21. The dental device of claim 20, wherein the biofilm-responsive overcoating comprises a particulate abrasive selected from the group of dental abrasives consisting of silica, pumice, alumina, calcium carbonate, dicalcium phosphate dihydrate and mixtures thereof;
 i. wherein said particulate abrasive:
  (a) is present at between about 2 and about 45 percent by weight of said device;
  (b) has a particle size between about 7 microns and about 200 microns; and
  (c) has a particulate size distribution from between about 5 microns and about 300 microns;
 ii. wherein said saliva soluble coated and particulate abrasive overcoated dental device substrate, when used as a dental device:
  (a) removes bioflim; and
  (b) indicates an Incidental Release Factor (IRF) of at least about 85 percent by weight.

* * * * *